United States Patent [19]

Nagareda et al.

[11] Patent Number: 5,973,208
[45] Date of Patent: Oct. 26, 1999

[54] PROCESS FOR PRODUCING DIAMINES

[75] Inventors: Katsushi Nagareda; Yoshihiro Tokuda, both of Okayama-ken; Shigeaki Suzuki, Osaka, all of Japan

[73] Assignee: Kuraray Co., Ltd., Kurashiki, Japan

[21] Appl. No.: 09/078,502

[22] Filed: May 14, 1998

[30] Foreign Application Priority Data

May 14, 1997 [JP] Japan ................................ 9-123867

[51] Int. Cl.$^6$ ................................................ C07C 209/26
[52] U.S. Cl. ........................................................ 564/473
[58] Field of Search ............................................. 564/473

[56] References Cited

U.S. PATENT DOCUMENTS

| | | |
|---|---|---|
| 2,636,051 | 4/1953 | Whetstone et al. . |
| 4,197,260 | 4/1980 | Siclari et al. . |
| 4,218,399 | 8/1980 | Siclari et al. . |
| 5,055,618 | 10/1991 | Kampmann et al. . |
| 5,475,141 | 12/1995 | Kos et al. . |

FOREIGN PATENT DOCUMENTS

| | | |
|---|---|---|
| 0 628 535 | 12/1994 | European Pat. Off. . |
| 2 328 692 | 5/1977 | France . |
| 2 418 219 | 9/1979 | France . |

OTHER PUBLICATIONS

Database WPI, Derwent Publications, AN 95–299534, JP 7–196586, Aug. 01, 1995.

Database WPI, Derwent Publications, AN 93–071072, JP 5–017413, Jan. 26, 1993.

*Primary Examiner*—Brian M. Burn
*Attorney, Agent, or Firm*—Oblon, Spivak, McClelland, Maier & Neustadt, P.C.

[57] ABSTRACT

A process for producing diamines by reacting a dialdehyde with ammonia and hydrogen in the presence of a hydrogenation catalyst to produce the corresponding diamine, where a solvent comprising an alcohol is used in the reaction and the concentration of water in the reaction mixture is 5 to 15% by weight.

13 Claims, No Drawings

PROCESS FOR PRODUCING DIAMINES

BACKGROUND OF THE INVENTION

1. Field of the Invention

The present invention relates to a process for producing diamines which are useful as, for example, starting materials for various polyamides and polyurethanes.

2. Description of the Background Art

Several processes for producing diamines are known, including feeding a solution obtained by dissolving a dialdehyde in a solvent to a reactor where a hydrogenation catalyst, the solvent, ammonia and hydrogen are present, and subjecting the dialdehyde to reductive amination to obtain the corresponding diamine. These processes include: (1) introducing a dialdehyde into a reactor for reductive amination at a rate which is not substantially higher than the consumption rate of the dialdehyde (see U.S. Pat. No. 2,636,051); (2) hemiacetalizing a dialdehyde by dissolving it in an alcoholic solvent and introducing the resulting solution into a reactor for reductive amination (see Japanese Patent Application Laid-open No. 17413/1993); and (3) mixing a dialdehyde with a diluting agent such as an alcohol while maintaining the mixing temperature at not more than 5° C., thereby suppressing formation of hemiacetal, and then feeding the mixture obtained to a reactor for amination (see Japanese Patent Application Laid-open No. 69999/1995).

In addition, one of the present inventors has found (4) a process which comprises, in the reductive amination of a dialdehyde effected by feeding a solution obtained by dissolving the dialdehyde in a solvent to a reactor where a hydrogenation catalyst, the solvent, ammonia and hydrogen are present, using a nickel catalyst carried on an inorganic oxide as the hydrogenation catalyst. In this process the catalyst may be re-used and can produce diamines in one step and at a high yield and low cost. See Japanese Patent Application Laid-open No. 196586/1995.

The above process (1) discloses Examples where water and Raney nickel are used as the solvent and catalyst, respectively. This process, however, where the yield of diamine is as low as not more than 40%, cannot be a commercial process in view of economy.

The above process (2) discloses an example where methanol or ethanol and Raney nickel are used as the solvent and catalyst, respectively, and can produce a diamine at a high yield of about 90%. However, according to a follow-up test conducted by the present inventors (Comparative Example 7 of the present specification), the Raney nickel used in the reaction markedly decreases in its catalytic activity, thereby causing problems when the recovered catalyst is to be re-used. This process cannot be economical in view of catalyst cost.

The above process (3) requires temperature control to suppress formation of hemiacetal. Cooling with a coolant should become necessary to this end, which is not favorable commercially.

With respect to the above process (4), the specification discloses in its Example 10 the reaction results when the catalyst was re-used. However, there the catalyst was re-used only once. The specification does not describe about the reaction results when the catalyst was repeatedly re-used or used continuously. The present inventors have studied repeated re-use of the catalyst in the process (4) (Comparative Example 1 of the present specification). In this case, the diamine yield decreased from 92% on the first use and 91% on the second use to as low as 82% on the fifth use. Accordingly, with this process (4) the diamine yield decreases on repeated re-use of the catalyst, which means that the process has a problem when used in a commercial production of diamines where the catalyst is continuously used.

Accordingly, an object of the present invention is to provide a process for producing diamines from the corresponding dialdehydes in one step and at a high yield and a cost lower than that with the conventional processes.

Reductive amination generally produces water as a by-product, which means that water is present in the reaction zone. Among the above-cited literature, only (3) Japanese Patent Application Laid-open No. 69999/1995 refers to this water by-product. Even this literature gives only the description in its Example 1 "the reaction water that formed is distilled" on work-up procedure after the reaction. With this type of description, it cannot be considered that water is recognized as having any influence on the reaction results. Although the disclosure gives no description about the water concentration during the reaction, the concentration is estimated to be 3.3% by weight at maximum from reaction conditions described therein.

U.S. Pat. No. 2,636,051 (i.e., (1)), all Examples of which use water as solvent, naturally gives no description about the water by-product. With (2) Japanese Patent Application Laid-Open No. 17413/1993, the amount of water by-product is, from the reaction conditions described in its Example 1, found by calculation to be 3.4% by weight. With (4) Japanese Patent Application Laid-open No. 196586/1995, the amount of water by-product is, from the reaction conditions described in its Example 1, found by calculation to be 2.30% by weight.

Accordingly, it is clear that none of the processes described above pay attention to the influence of water by-product on reductive amination, or refer to control of the concentration of water present in the reaction zone.

SUMMARY OF THE INVENTION

As the result of an intensive study on the influence on the reaction results of the water concentration in the reductive amination reaction mixture, the present inventors have found a process for producing diamines by feeding a dialdehyde or a solution obtained by dissolving the dialdehyde in a solvent to a reactor where a hydrogenation catalyst, the solvent, ammonia and hydrogen are present and subjecting the dialdehyde to reductive amination reaction to obtain the corresponding diamine. In the present process, an alcohol is used as the solvent and the water concentration is maintained in the reaction mixture at 5 to 15% by weight.

According to the process of the present invention, which can markedly suppress the decrease of the activity of the catalyst during reductive amination, diamines may be produced at low cost. That the use of an alcoholic solvent and the maintenance of the water concentration in the reaction mixture at 5 to 15% by weight can suppress the decrease of the catalyst activity is a new finding, having never been recognized or described in the publications described above. With a process for producing expensive diamines, a low yield due to decrease of the catalyst activity gives a large, negative influence on their production costs and decreases the commercial value of the process. Furthermore, with a process for the continuous production of diamines, frequent renewal of the catalyst used necessitated by the decrease of the catalyst activity requires a complex procedure, thereby decreasing the commercial value of the process. The process of the present invention, which can suppress decrease of the catalyst activity, can solve these problems on commercial production and is thus much improved as compared to the conventional processes described above.

A more complete appreciation of the invention and many of the attendant advantages thereof will be readily obtained as the same becomes better understood by reference to the following detailed description.

DETAILED DESCRIPTION OF INVENTION

Examples of the dialdehydes used in the present invention include dialdehydes having skeletons of linear and branched aliphatic hydrocarbons, alicyclic hydrocarbons and aromatic hydrocarbons having 4 to 20, preferably 6 to 16, more preferably 8 to 12 carbon atoms. Examples of suitable aldehydes are, for example, linear aliphatic dialdehydes, e.g., butanedial, hexanedial, octanedial, nonanedial, decanedial, undecanedial, dodecanedial, tetradecanedial, hexadecanedial, octadecanedial and eicosanedial; branched aliphatic dials, e.g., 2-methyloctanedial, 2-methylnonanedial and 2,7-dimethyloctanedial; alicyclic dials, e.g., 1,3-cyclohexanedicarbaldehyde, 1,4-cyclohexanedicarbaldehyde, 3(4),8(9)-tricyclo [5.2.1.0] decanedicarbaldehyde and 2(3),5(6)-bicyclo[2.2.1] heptanedicarbaldehyde; and aromatic dialdehydes, e.g., terephthalaldehyde and isophthalaldehyde. These aldehydes can be readily and at a low cost synthesized by conducting an oxo reaction of unsaturated aldehydes having carbon atoms in a number smaller by 1 or diolefins having carbon atoms in a number smaller by 2. They can also be obtained from cyclic olefins having the same number of carbon atoms by ozonolysis and the succeeding reduction, from aromatic hydrocarbons having the same number of carbon atoms by oxidation and from dicarboxylic acids having the same number of carbon atoms by reduction.

It is desirable that the reactions be effected with the dialdehyde used having a concentration of 5 to 25% by weight based on the weight of total reaction liquid. This range includes all specific values and subranges therebetween, including 8, 10, 12, 15 and 20% by weight. With the concentration being not more than 5% by weight, large amounts of the ammonia and solvent are recovered in the separation and purification processes of the obtained diamine, so that the process becomes of small commercial value. On the other hand, if the concentration exceeds 25% by weight, there will be formed a large amount of polymers, which decreases the yield of the diamine and deteriorates the catalyst used.

From the above starting material dialdehydes, there are obtained, correspondingly, linear aliphatic diamines, e.g., butanediamine, hexanediamine, octanediamine, nonanediamine, decanediamine, undecanediamine, dodecanediamine, tetradecanediamine, hexadecanediamine, octadecanediamine and eicosanediamine; branched aliphatic diamines, e.g., 2-methyloctanediamine, 2-methylnonanediamine and 2,7-dimethyloctanediamine; alicyclic diamines, e.g., 1,3-cyclohexanedimethanamine, 1,4-cyclohexanedimethanamine, 3(4),8(9)-tricyclo[5.2.1.0] decanedimethanamie and 2(3),5(6)-bicyclo[2.2.1]heptane-dimethanamine; and aromatic diamines, e.g., p-xylylenediamine and m-xylylenediamine.

The alcoholic solvent used in the invention includes alcohols, diols and polyols. The alcohols include aliphatic, alicyclic and aromatic alcohols. The alcoholic solvent preferably has not more than 10 carbon atoms. Examples of suitable alcohols are, for example, aliphatic alcohols, e.g., methanol, ethanol, n-propyl alcohol, i-propyl alcohol, n-butyl alcohol, i-butyl alcohol, sec-butyl alcohol, tert-butyl alcohol, n-amyl alcohol, i-amyl alcohol, sec-amyl alcohol, tert-amyl alcohol, n-hexanol, n-heptanol, n-octanol, n-decanol, 2-ethylhexanol, 2-octanol, 3-octanol; alicyclic alcohols, e.g., cyclohexanol, cyclohexylmethanol, 2-cyclohexylethanol and 1-cyclohexylethanol; and aromatic alcohols, e.g., benzyl alcohol and 2-phenylethanol; diols, e.g., ethylene glycol, 1,2-propanediol, 1,3-propanediol, 1,3-butanediol, 2-methyl-1,3-propanediol, 1,4-butanediol, 2-methyl-1,4-butanediol, 1,5-pentanediol, 3-methyl-1,5-pentanediol, 1,6-hexanediol and diethylene glycol; and polyols, e.g., glycerine and pentaerythritol. Among these alcoholic solvents having not more than 10 carbon atoms, aliphatic alcohols having not more than 5 carbon atoms are particularly preferred, since they have good distillation-separability from the diamines that are formed. These alcoholic solvents may be used singly or in appropriate admixtures of 2 or more.

If an alcoholic solvent having not less than 11 carbon atoms is used, the solubility in the solvent itself of water and ammonia may become low, so that the reactions cannot be effected in a homogeneous phase. Besides, such alcohols are expensive, so that the process decreases in its commercial value.

There are no particular restrictions with respect to the amount of the alcoholic solvent used. The solvent is generally used in an amount of 0.5 to 20 parts by weight based on the weight of the dialdehyde used, preferably 1 to 10 parts by weight on the same basis. These ranges include all specific values and subranges therebetween, including 2, 5, 8, 12 and 15 parts by weight. Too large an amount of the alcoholic solvent is disadvantageous in practice in view of recovery and re-use of the solvent, while too small an amount thereof leads to decreased yield of the resulting diamine and to serious deterioration of the catalyst used.

In the present invention, the concentration of water present in the reaction zone is maintained at 5 to 15% by weight based on the total weight of the reaction mixture, preferably at 7 to 12% by weight on the same basis. These ranges include all specific values and subranges therebetween, including 6, 8 and 10% by weight. It is known, as described above, that with conventional processes of producing diamines by reductive amination of a dialdehyde, up to about 3.4% by weight of water forms as a result of condensation of the dialdehyde with ammonia. On the other hand, according to the present invention, the water concentration in the reductive amination reaction mixture is, if necessary by addition of water from outside the reaction zone, maintained within a range of 5 to 15%. If the water concentration is less than 5% by weight, there will be produced no appreciable effect of suppressing adhesion of high boiling components onto the surface of the catalyst used, which deteriorates the catalyst activity. On the other hand, if the water concentration exceeds 15% by weight, the aldehyde groups of the starting material dialdehyde will be partially hydrogenated. The amount of the byproducts thus produced will then increase and hence the selectivity will decrease. Besides, the increased amount of the resulting high boiling components will deactivate the catalyst, which also leads to a decrease in the yield.

The ammonia for the reductive amination is generally used in an amount of ammonia in the reaction liquid of 5 to 50 molar equivalents based on the moles of the starting material dialdehyde, preferably 10 to 30 molar equivalents on the same basis. These ranges include all specific values and subranges therebetween. Too little ammonia decreases the yield, while too much ammonia is disadvantageous for practical purposes.

The reductive amination that produces diamines from the corresponding dialdehydes may be carried out by the usual processes. Examples of the catalyst usable for this purpose are Raney catalysts, e.g., Raney nickel, Raney cobalt and Raney copper; and carried catalysts comprising metals having hydrogenation activity, e.g., nickel, cobalt, platinum, palladium, rhodium, ruthenium and copper, carried on a carrier, such as diatomaceous earth, silica, alumina, silica alumina, clay, titania, zirconia, magnesia, calcia, lanthanum oxide, niobium oxide or carbon. Among these, nickel catalysts such as those carried on inorganic oxides or Raney nickel are preferred. Here, the carriers used may contain alkali metals, alkali earth metals, oxides of phosphine or mixtures of the foregoing. Although preferred catalysts principally comprise nickel, they may contain nickel alone or may be modified with another metal or metals such as cobalt, iron, copper, chromium, manganese, silver, molybdenum, rhenium, palladium, rhodium, ruthenium and platinum. The amount of the nickel catalyst used can vary according to the desired reaction rate, and is generally selected from the range of 0.01 to 30% by weight based on the total weight of reaction liquid, preferably from the range of 0.1 to 10% by weight on the same basis. These ranges include all specific values and subranges therebetween. The catalyst may be dispersed in the reaction liquid phase or used as a fixed bed.

The reductive amination is effected generally at a temperature of 40 to 200° C., preferably 80 to 160° C., more preferably 100 to 140° C. These temperature ranges include all specific values and subranges therebetween. If the reaction temperature is lower than 40° C., the reactions will not proceed at a commercially satisfactory rate. If the reaction temperature exceeds 200° C., byproducts will form in large amounts, thereby decreasing the yield.

The reaction pressure, to which no specific limitation is placed, is generally in a range of 40 to 200 atm, inclusive of all specific values and subranges therebetween. Hydrogen may be added to make up the amount consumed during the reaction, or it may be constantly circulated during the reaction.

The reaction can be carried out by batch or continuous system. It is recommended to feed the dialdehyde used to the reactor at a rate lower than the hydrogenation rate. That is, where a batch-type reactor is used, it is desirable to effect the reaction while feeding a dialdehyde or a solution of the dialdehyde dissolved in a solvent to the reactor filled with a catalyst, the solvent, ammonia and hydrogen, at a rate lower than the hydrogenation rate. With a continuous system, it is desirable to effect the reaction while feeding ammonia, solvent and dialdehyde to a reactor filled with a catalyst, solvent and hydrogen.

The catalyst used can be re-used by withdrawing the reaction mixture alone, by filtration, centrifugal separation or like methods, or by withdrawing the reaction mixture containing the catalyst from the reactor, then separating the catalyst by the same method and then returning it to the reactor.

In one embodiment, the catalyst is isolated from the first reaction mixture and used in a second reaction. Preferably, the yield of diamine in the second reaction is at most 5% less than the diamine yield in the first reaction. More preferably, the yield of diamine in the second reaction is at most 4, 3, or 2% less than the diamine yield in the first reaction, or the diamine yield is the same in the first and second reactions. In another embodiment, the catalyst is isolated from the reaction mixture and reused a plurality of times, e.g., up to five, ten, or more times.

In another embodiment, when the reaction is conducted continuously, i.e., the mixture of the dialdehyde, solvent and water is added to the reaction zone and almost the same quantity of the reaction mixture is removed simultaneously, it is preferred that the yield of diamine obtained after conducting the process for more than 1 hour is at most 20% less as compared to the diamine yield obtained at 1 hour. More preferably, the yield of diamine obtained after conducting the process for more than 1 hour is at most 10% less as compared to the diamine yield obtained at 1 hour. Most preferably, the yield of diamine obtained after conducting the process for more than 1 hour is at most 8% less as compared to the diamine yield obtained at 1 hour.

The yield of the diamine is, of course, preferably as high as possible. Preferably, the diamine yield is at least 80%, based on the dialdehyde. More preferably, the diamine yield is at least 90%, based on the dialdehyde. Still m ore preferably, the diamine yield is at least 95%, based on the dialdehyde. Most preferably, the diamine yield is at least 95 to 100%, based on the dialdehyde.

The diamine thus obtained can be purified to a high purity by the usual purification procedure comprising distilling off ammonia and solvent from the reaction mixture from which the catalyst has been separated and subjecting the residue to distillation or recrystallization.

Other features of the invention will become apparent in the course of the following descriptions of exemplary embodiments which are given for illustration of the invention and are not intending to be limiting thereof.

EXAMPLES

Example 1

A 500-ml autoclave equipped with an electromagnetic stirrer was charged with 1.5 g of a nickel catalyst and 70.0 g of n-butanol. The air in the autoclave was then replaced by hydrogen under a hydrogen pressure of 10 kg/cm$^2$ three times. Thereafter, 62.5 g of ammonia was added and hydrogen was added to a pressure of 50 kg/cm$^2$, and the autoclave was heated to a temperature of 140° C. After the total inside pressure had been adjusted by hydrogen to 100 kg/cm$^2$, a mixed solution containing 37.5 g of a 80/20 by moles mixed liquid of 1,9-nonanedial and 2-methyl-1,8-octanedial, 70.0 g of n-butanol and 10.0 g of water was fed over 1 hour to the autoclave, and reaction was carried out for 2 hours. During the reaction, hydrogen was successively supplied such that the total pressure inside the autoclave was maintained at 100 kg/cm$^2$. The concentration of water in the reaction mixture, which was the sum of the water formed by condensation of the dialdehydes and ammonia and the water added from outside, was 7.5% by weight. After completion of the reaction, the autoclave was allowed to cool and unreacted ammonia was released. The contents were then separated from the catalyst by filtration, to give 136.2 g of the reaction mixture containing diamines. Gas chromatography of the reaction mixture revealed that 36.5 g of a 80/20 (by moles) mixture of 1,9-nonanediamine and 1,8-octanediamine and 0.2 g of byproduced amines having hydroxyl group on one end thereof. The yield of the diamines based on the dialdehydes fed was found by calculation to be 96%.

The above reactions were repeated with use of the catalyst separated by filtration above. Gas chromatography of the reaction mixture after separation of the catalyst revealed that the yield of the diamines based on the dialdehydes fed was 94%.

In the same manner, the reactions were repeated for the 3rd, 4th and 5th times. The corresponding yields of the diamines were 94%, 92% and 91%.

In the 5 repeated reactions, the decrease of the diamine yield was only 5%, which proves a very low degree of deterioration of the catalyst.

Comparative Example 1

A test for using a catalyst repeatedly was carried out following the procedure below, while reference was made to Example 1 of the Japanese Patent Application Laid-open No. 196586/1995.

A 300-ml autoclave equipped with an electromagnetic stirrer was charged with 1.15 g of a nickel catalyst (nickel content: 52%) carried on diatomaceous earth having a porosity of 0.19 ml/g with pores having a diameter of about 10 to about 100 nm and 63.0 g of n-butanol. Hydrogen was then introduced under a pressure of 60 atm. Thereafter, the contents were heated to a temperature of 160° C. and reduction was effected with the catalyst at this temperature for 20 minutes. The autoclave was allowed to cool down to room temperature and the hydrogen released. Next, 30.6 g of ammonia was fed and the temperature was raised to 160° C. under a hydrogen pressure of 30 atm. A solution of 18.72 g of a mixture of 1,9-nonanedial and 2-methyl-1,8-octanedial in 70.0 g of n-butanol was, while hydrogen was streamed at a rate of 20 l/hour, fed with a high-pressure metering pump over 40 minutes. After completion of the feeding, hydrogen was further streamed at 160° C. for 1 hour with stirring.

The water concentration in the reaction mixture became 2.3% by weight, as constituted by the condensed water of the dialdehydes and ammonia The concentration of the dialdehyde fed in the total reaction liquid was 10% by weight.

After stoppage of the hydrogen flow, the autoclave was allowed to cool and the pressure released to atmospheric pressure. Removal of the catalyst by filtration and condensation of the filtrate gave 18.8 g of a crude product. Gas chromatography revealed that the crude product containing 17.5 g of a mixture of 1,9-nonanediamine and 2-methyl-1,8-octanediamine, which indicates that the total yield of the diamines was 92.3%.

The above procedure was repeated 5 times with use of the catalyst separated by filtration above and the change of the diamine yield was studied. The results of the 5 repeated reactions are shown below.

| 1st reaction: Diamine yield | 92% |
| 2nd reaction: Diamine yield | 91% |
| 3rd reaction: Diamine yield | 89% |
| 4th reaction: Diamine yield | 86% |
| 5th reaction: Diamine yield | 82% |

In the 5 repeated reactions, the diamine yield decreased from 92% of the first time to 82% for the last, i.e., decreased by 10%, thus proving a higher degree of deterioration of the catalyst as compared with that in Example 1.

Example 2

Example 1 was repeated except that 70.0 g of methanol was used instead of 70.0 g of n-butanol fed together with the catalyst and that 70.0 g of methanol was used instead of 70.0 g of n-butanol of the mixed solution fed. The concentration of water in the reaction mixture, which was the sum of the water formed by condensation of the dialdehydes and ammonia and the water added from outside, was 7.5% by weight. The results of the 5 repeated reactions are shown below.

In the 5 repeated reactions, the decrease of the diamine yield was only 5%, which proves a very low degree of deterioration of the catalyst.

| 1st reaction: Diamine yield | 95% |
| 2nd reaction: Diamine yield | 94% |
| 3rd reaction: Diamine yield | 92% |
| 4th reaction: Diamine yield | 92% |
| 5th reaction: Diamine yield | 90% |

Example 3

Example 1 was repeated except that 70.0 g of i-amyl alcohol was used instead of 70.0 g of n-butanol fed together with the catalyst and that 70.0 g of i-amyl alcohol was used instead of 70.0 g of n-butanol of the mixed solution fed. The concentration of water in the reaction mixture, which was the sum of the water formed by condensation of the dialdehydes and ammonia and the water added from outside, was 7.5% by weight. The results of the 5 repeated reactions are shown below.

In the 5 repeated reactions, the decrease of the diamine yield was only 4%, which proves a very low degree of deterioration of the catalyst.

| 1st reaction: Diamine yield | 95% |
| 2nd reaction: Diamine yield | 95% |
| 3rd reaction: Diamine yield | 93% |
| 4th reaction: Diamine yield | 92% |
| 5th reaction: Diamine yield | 91% |

Example 4

Example 1 was repeated except that the amounts of n-butanol and water of the mixed solution fed were changed from 70.0 g to 60.0 g and from 10.0 g to 20.0 g, respectively. The concentration of water in the reaction mixture, which was the sum of the water formed by condensation of the dialdehydes and ammonia and the water added from outside, was 11.5% by weight. The results of the 5 repeated reactions are shown below.

In the 5 repeated reactions, the decrease of the diamine yield was only 6%, which proves a very low degree of deterioration of the catalyst.

| 1st reaction: Diamine yield | 94% |
| 2nd reaction: Diamine yield | 93% |
| 3rd reaction: Diamine yield | 92% |
| 4th reaction: Diamine yield | 90% |
| 5th reaction: Diamine yield | 88% |

Comparative Example 2

Example 1 was repeated except that water was not added to the mixed solution fed and that the amount of n-butanol of the mixed solution fed was changed from 70.0 g to 80.0 g. The concentration of water in the reaction mixture, as formed by condensation of the dialdehydes and ammonia, was 3.5% by weight. The results of the 5 repeated reactions are shown below.

In the 5 repeated reactions, the decrease of the diamine yield was 11%, which shows a higher degree of deterioration of the catalyst as compared with the case where water was added.

| | |
|---|---|
| 1st reaction: Diamine yield | 96% |
| 2nd reaction: Diamine yield | 92% |
| 3rd reaction: Diamine yield | 91% |
| 4th reaction: Diamine yield | 88% |
| 5th reaction: Diamine yield | 85% |

Comparative Example 3

Example 1 was repeated except that the amount of n-butanol initially fed was changed from 70.0 g to 50.0 g and that the amounts of n-butanol and water of the mixed solution fed were changed from 70.0 g to 60.0 g and from 10.0 g to 20.0 g, respectively. The concentration of water in the reaction mixture, which was the sum of the water formed by condensation of the dialdehydes and ammonia and the water added from outside, was 19.5% by weight. The results of the 5 repeated reactions are shown below.

During the 5 repeated reactions, the diamine yield decreased to a large extent and white polymers generated. The degree of deterioration of the catalyst was higher than that in the case where water was added in a smaller amount.

| | |
|---|---|
| 1st reaction: Diamine yield | 84% |
| 2nd reaction: Diamine yield | 76% |
| 3rd reaction: Diamine yield | 62% |
| 4th reaction: Diamine yield | 48% |
| 5th reaction: Diamine yield | 23% |

Comparative Example 4

Example 1 was repeated except that 70.0 of tetrahydrofuran was used instead of 70.0 g of n-butanol fed together with the catalyst and that 70.0 g of tetrahydrofuran was used instead of 70.0 g of n-butanol of the mixed solution fed. The concentration of water in the reaction mixture, which was the sum of the water formed by condensation of the dialdehydes and ammonia and the water added from outside, was 7.5% by weight. The results of the 5 repeated reactions are shown below.

During the 5 repeated reactions, the diamine yield decreased by 21%, which shows that the degree of deterioration of the catalyst was higher than that in the case where butanol was used as solvent.

| | |
|---|---|
| 1st reaction: Diamine yield | 94% |
| 2nd reaction: Diamine yield | 90% |
| 3rd reaction: Diamine yield | 85% |
| 4th reaction: Diamine yield | 81% |
| 5th reaction: Diamine yield | 73% |

Example 5

Example 1 was repeated except that 37.5 of 3(4),8(9)-tricyclo[5.2.1.0]decane-dicarbaldehyde was used instead of 37.5 g of the mixture of 1,9-nonanedial and 1,8-octanedial (80/20 molar ratio). The concentration of water in the reaction mixture, which was the sum of the water formed by condensation of the dialdehydes and ammonia and the water added from outside, was 6.8% by weight. The results of the repeated reactions are shown below.

In the 5 repeated reactions, the decrease of the diamine yield was only 3%, which proves a very low degree of deterioration of the catalyst.

| | |
|---|---|
| 1st reaction: Diamine yield | 96% |
| 2nd reaction: Diamine yield | 95% |
| 3rd reaction: Diamine yield | 95% |
| 4th reaction: Diamine yield | 93% |
| 5th reaction: Diamine yield | 93% |

Example 6

A 100-ml autoclave equipped with an electromagnetic stirrer was charged with 1.44 g of a nickel catalyst, 21.0 g of n-butanol and 3.5 g of water. The air in the autoclave was then replaced by hydrogen under a hydrogen pressure of 10 kg/cm$^2$ three times. Thereafter, 10.5 g of ammonia was added and hydrogen was added to a pressure of 50 kg/cm$^2$, and the autoclave was heated to a temperature of 140° C. After the total inside pressure had been adjusted by hydrogen to 100 kg/cm$^2$, a mixed solution containing 8.75 parts by weight of a 80/20 by moles mixed liquid of 1,9-nonanedial and 2-methyl-1,8-octanedial, 19.52 parts by weight of n-butanol and 2.36 parts by weight of water was fed to the reactor at a rate of 30.63 g/hr. At the same time, ammonia and hydrogen were also fed at rates of 13.13 g/hr and 10 l/hr, respectively. Continuous reaction was effected, while the reaction mixture was withdrawn through a sampling port fitted with a mesh filter to keep the reaction liquid in the reactor at a volume of 50 ml. The concentration of water in the reaction mixture, which was the sum of the water formed by condensation of the dialdehydes and ammonia and the water added initially and fed from outside, was 10.0% by weight. Every one hour, portions of the withdrawn reaction mixture were, after removal of ammonia by evaporation, subjected to gas chromatography. The diamine yield was found to change as follows.

After 20 hours, the yield was, although with 7% decrease, maintained at a good level. The total production of the diamines by this 20-hour reactions was 161.3 g, and the average yield was 91%. This means that the catalyst consumption per 1 kg of diamine was 8.9 g.

| | | |
|---|---|---|
| After 1 hour | Diamine yield | 94% |
| After 2 hours, | Diamine yield | 96% |
| After 3 hours: | Diamine yield | 93% |
| After 4 hours: | Diamine yield | 93% |
| After 5 hours: | Diamine yield | 94% |
| After 10 hours: | Diamine yield | 92% |
| After 15 hours: | Diamine yield | 90% |
| After 20 hours: | Diamine yield | 87% |

Comparative Example 5

Example 6 was repeated except that the amount of n-butanol fed together with the catalyst was changed from 21.0 to 24.5 g, that no water wad added initially, that the amount of n-butanol of the mixed solution fed to the reactor was changed from 19.52 parts by weight to 26.58 parts by weight and that no water was added to the mixed solution, to effect continuous reactions. The solution was fed at the same feed rate of 30.63 g/hr as that in Example 6. The concentration of water in the reaction mixture, which originated only from the water formed by condensation of the dialdehydes and ammonia, was 4.0% by weight. The results of the 20-hour reactions are shown below. After 20 hours the yield decreased by 23%.

Comparative Example 6

Example 6 was repeated except that the amounts of the n-butanol and water fed together with the catalyst were changed from 21.0 to 18.2 g and from 3.5 g to 5.86 g, respectively, and that the amounts of n-butanol and water of the mixed solution fed to the reactor were changed from 19.52 parts by weight to 16.02 parts by weight and from 2.36 parts by weight to 5.86 parts by weight, respectively, to effect continuous reactions. The solution was fed at the same feed rate of 30.63 g/hr as that in Example 6. The concentration of water in the reaction mixture, inclusive of the water formed by condensation of the dialdehydes and ammonia, was 18.0% by weight. The yield after 18 hours was 51%, thus showing 43% decrease in 18 hours.

Table 1 summarizes the results obtained in Example 6 and Comparative Examples 5 and 6.

TABLE 1

|  | Example 6 | Comparative Example 5 | Comparative Example 6 |
|---|---|---|---|
| Water concentration | 10.0% | 4.0% | 18.0% |
| Yield after: | | | |
| 1 hour | 94% | 95% | 94% |
| 2 hours | 96% | 95% | 93% |
| 3 hours | 93% | 93% | 92% |
| 4 hours | 93% | 92% | 92% |
| 5 hours | 94% | 91% | 90% |
| 10 hours | 92% | 86% | 83% |
| 15 hours | 90% | 80% | 64% |
| 20 hours | 87% | 72% | Reaction could not be continued |
| Decrease of yield from 1-hour value | 7% | 23% | >43% |
| Average yield | 91% | 85% | 76% |
| Amt. of diamines produced | 161.3 g | 130.1 g | 134.7 g |
| Catalyst consumption/kg | 8.9 g | 11.1 g | 10.7 g |

Comparative Example 7

A test for using a catalyst repeatedly was carried out following the procedure below, in accordance with Example 1 of the Japanese Patent Application Laid-open No. 196586/1995.

A 500-ml autoclave equipped with an electromagnetic stirrer was charged with 76 g of methanol. 7.5 g of Raney nickel and 59.5 g of ammonia. Hydrogen was introduced to a pressure of 15 kg/cm$^2$ and the autoclave was heated, After the inside temperature of the autoclave had reached 120° C., hydrogen was further introduced to an inside pressure of 40 kg/cm$^2$. Thereafter, 119 g of a methanolic solution obtained by dissolving 27.3 of 1,9-nonanedial and 11.7 g of 2-methyl-1,8-octanedial in 80.0 g of methanol was fed into the autoclave with a high-pressure metering pump over 3 hours. During the feeding of the methanolic solution, the inside of the autoclave was kept at a temperature of 120° C. Simultaneously with the stoppage of feeding the methanolic solution, the consumption of hydrogen stopped and the reaction terminated. The reaction mixture was allowed to cool, and then the catalyst was separated by filtration. Gas chromatography revealed that there was obtained 35.6 g of a mixture of 1,9-nonanediamine and 2-methyl-1,8-octanediamine. The yield of the obtained diamines based on the total dialdehydes fed was found by calculation to be 90%.

The same procedure as above except that the catalyst recovered by filtration was used instead of 7.5 g of Raney nickel was followed for further 4 times, and the change of the diamine yield was studied. The results are shown below.

| 1st reaction: Diamine yield | 90% |
|---|---|
| 2nd reaction: Diamine yield | 85% |
| 3rd reaction:Diamine yield | 78% |
| 4th reaction: Diamine yield | 65% |
| 5th reaction: Diamine yield | 48% |

In the re-use test of the recovered Raney nickel catalyst, the activity after the reaction decreased markedly.

Obviously, numerous modifications and variations of the invention are possible in light of the above teachings. It is therefore to be understood that within the scope of the appended claims, the invention may be practiced otherwise than as specifically herein.

Japanese Patent Application 123867/1997, filed May 14, 1997, is incorporated herein by reference in its entirety.

We claim:

1. A process for producing diamines, comprising:

reacting a dialdehyde with ammonia and hydrogen in the presence of a hydrogenation catalyst to produce the corresponding diamine, wherein a solvent comprising an alcohol is used in the reaction and the concentration of water in the reaction mixture is 5 to 15% by weight.

2. The process of claim 1, wherein the alcohol is a diol or a polyol.

3. The process of claim 1, wherein the alcohol is an aliphatic alcohol having at most 5 carbon atoms.

4. The process of claim 1, wherein the dialdehyde is nonanedial, 2-methyloctanedial or a mixture thereof.

5. The process of claim 1, wherein the concentration of water in the reaction mixture is 7 to 12% by weight.

6. The process of claim 1, wherein the hydrogenation catalyst comprises at least one metal selected from the group consisting of nickel, cobalt, platinum, palladium, rhodium, ruthenium and copper.

7. The process of claim 1, wherein the hydrogenation catalyst is a nickel catalyst supported on an inorganic oxide, or is Raney nickel.

8. The process of claim 1, wherein the dialdehyde has 4 to 20 carbon atoms.

9. The process of claim 1, wherein the reaction is conducted at a temperature of 40 to 200° C.

10. The process of claim 1, wherein the alcohol has at most 10 carbon atoms.

11. The process of claim 1, wherein the yield of the diamine is at least 80% based on the amount of the dialdehyde.

12. The process of claim 1, further comprising isolating the diamine from the reaction mixture.

13. The process of claim 1, further comprising isolating the diamine from the reaction mixture, followed by purifying the isolated diamine by distillation or recrystallization.

* * * * *